(12) United States Patent
Yunoki et al.

(10) Patent No.: US 8,389,010 B2
(45) Date of Patent: Mar. 5, 2013

(54) STRETCHABLE COLLAGEN MATERIAL AND MANUFACTURING METHOD AND USE THEREOF

(75) Inventors: Shuji Yunoki, Tsukuba (JP); Nobuhiro Nagai, Sapporo (JP)

(73) Assignee: Ihara & Company Ltd., Hokkaido (JP)

( * ) Notice: Subject to any disclaimer, the term of this patent is extended or adjusted under 35 U.S.C. 154(b) by 7 days.

(21) Appl. No.: 12/198,477

(22) Filed: Aug. 26, 2008

(65) Prior Publication Data
US 2009/0069540 A1 Mar. 12, 2009

Related U.S. Application Data

(63) Continuation-in-part of application No. 10/565,944, filed as application No. PCT/JP2005/008470 on Apr. 27, 2005, now abandoned.

(30) Foreign Application Priority Data

Apr. 28, 2004 (JP) .................................. 2004-133662
Feb. 15, 2005 (JP) .................................. 2005-037417

(51) Int. Cl.
  *A61L 15/32* (2006.01)
  *A61F 13/00* (2006.01)
  *C07K 14/78* (2006.01)
  *C07C 267/00* (2006.01)
(52) U.S. Cl. ........ 424/485; 424/443; 424/422; 530/356; 560/334
(58) Field of Classification Search .................. 424/485, 424/443, 422; 530/334, 356
See application file for complete search history.

(56) References Cited

U.S. PATENT DOCUMENTS

5,028,597 A * 7/1991 Kodama et al. ................. 514/56
5,714,582 A   2/1998 Wolfinbarger
6,541,023 B1 * 4/2003 Andre et al. .................. 424/422

FOREIGN PATENT DOCUMENTS

CA    2485914 A1   11/2003

OTHER PUBLICATIONS

Kadler et al., "Collagen fibril formation," Biochem J 316(1):1-11, 1996.*
Yunoki S et al; "Novel Biamaterial from Reinforced Salmon Collagen Gel Prepared by Fabril F . . . ";Journal of Bioscience and Bioengineering; Nol. 98, No. 1, 40-47; 2004.
Koide et al; Effects of Various Collagen Crosslinking Techniques on Mechancial . . . ; Dental Materials Journal 16; 1997; pp. 1-9.
Damink et al; Glutaraldehyde as a crosslinking agent for colagen-based . . . ; Journal of Materials Science: Materials in Medicine 6; 1995; 13 pages.
Daamen et al.; Preparation and evaluation of molecularly-defined . . . ; Biomaterials 24; 2003; pp. 4001-4009.
Yunoki et al; Novel elastic material from collagen for tissue engineering; J Mater Sci: Mater Med; 2007; 18; pp. 1369-1375.

* cited by examiner

*Primary Examiner* — Rosanne Kosson
(74) *Attorney, Agent, or Firm* — Novak Druce Connolly Bove + Quigg LLP

(57) ABSTRACT

The present invention provides a stretchable collagen material, particularly collagen derived from fishes, having excellent stretching property and mechanical strength, which can be widely used as a cell carrier and medical material, and to a method for manufacturing the same. By thermally treating a gel comprising collagen fiber cross-linked by using cross-linking agent, the collagen enhanced in both stretching property and mechanical strength can be produced. The stretchable collagen material is extremely useful as a cell carrier material and medical material.

9 Claims, 2 Drawing Sheets

Fig. 3
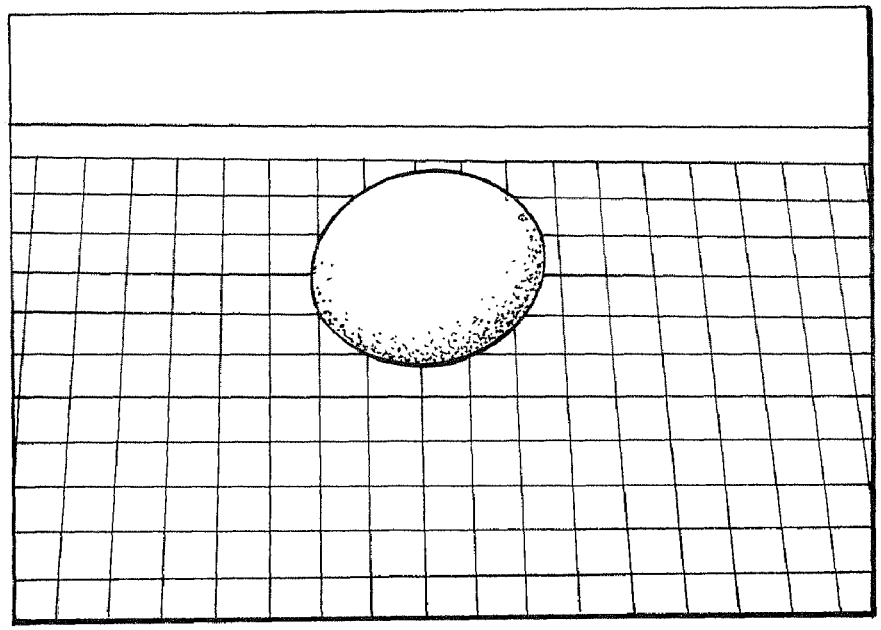
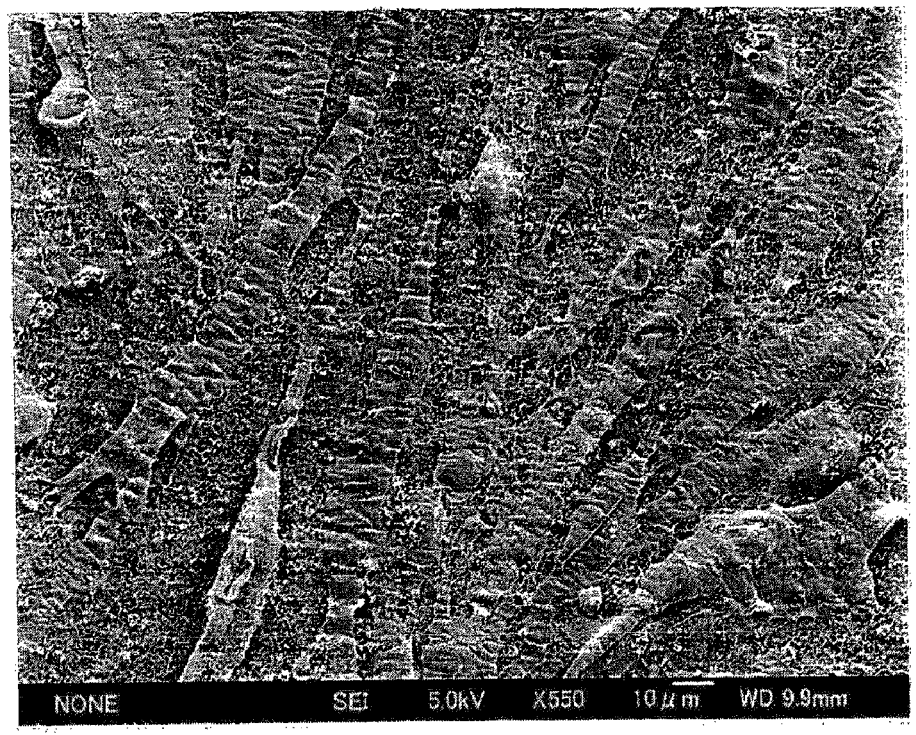
Fig. 4

STRETCHABLE COLLAGEN MATERIAL AND MANUFACTURING METHOD AND USE THEREOF

TECHNICAL FIELD

The present invention relates to a stretchable collagen material having a rubber-like property and to a method for manufacturing the same. More particularly, it relates to a stretchable collagen material prepared by a thermal treatment of gel formed through cross-linking of collagen fiber especially derived from fishes, to a method for manufacturing the same and to a cell carrier and a medical material using the same.

BACKGROUND ART

Collagen is defined as protein or glycoprotein having a helical structure (collagen helices) at least partially. This is a triple helix comprising three polypeptide chains and, in each polypeptide chain of a molecular weight of about 100,000, a glycine residue appears every three amino acid residues and, as for other amino acid residues, proline residues and hydroxyproline residues appear frequently. Collagen can be extracted mainly from tissues, particularly from skin, of invertebrate or vertebrate animals. 19 generic types of collagens, classified by molecule structure, have been reported and in some cases, one collagen type so classified includes several different molecule species.

Particularly, collagens of types I, II, III and IV are mainly used as starting materials for biomaterials. Type I is present inmost of connective tissues and is a collagen type which is most abundantly present in living organism. Type I is especially abundant in tendons, coria and bones and, collagens for industrial uses are extracted from those sites in many cases. Type II is collagen which forms cartilage. Type III is often present in the same site as the type I although its amount is small. Type IV is collagen which forms basement membrane. Types I, II and III are present in living organism as collagen fibers and mainly play a role of maintaining the strength of tissues or organs. Although type IV cannot form fiber, it is said to form a network assembly of four molecules and to participate in cell differentiation in basement membranes. The term "collagen(s)" used in the present specification as hereinafter means collagen of type I, II or III or a mixture of two or more types thereof.

Collagen fiber is a self-aggregate of the above-mentioned collagen and has a specific fiber structure in which collagen molecules are packed in series and also in parallel. Industrially, soluble collagen is manufactured from collagen fiber in tissues using acid, alkali or proteinase.

Soluble collagen comprises fine assemblies consisting of not more than several collagen molecules, whereby can form a uniform and transparent solution when dissolved in water or in an aqueous salt solution. It is known that collagen molecules, once solubilized, can recreate collagen fiber in vitro under certain conditions. Such a phenomenon is called fibril formation or fibrillation and its properties are described in detail in *Biochemical Journal*, 316, pages 1-11 (1996).

When collagen is heated, the triple helical structure of collagen is raveled out and each polypeptide chain gives a thermally denatured product in a random coil form. The temperature causing such a structural change is called a denaturing temperature and such a thermally denatured product is called gelatin. It is known that, as compared with collagen, gelatin has a high solubility in water and a high sensitivity to protease in living organisms. It is also known that, depending upon the condition concerning solvent, gelatin partially can recover the collagen helical structure and that although ability for forming collagen fiber in collagen has been lost in the denaturing process, by thus partially recovering the collagen helical structure in gelatin, the ability for formation of collagen fiber can also be recovered.

Denaturing temperature of collagen is lowest in a state of solution. It is also said that, although collagen is usually obtained from living materials, denaturing temperature of collagen obtained from living organisms is closely related to the temperature of living environment of the living organism. Denaturing temperature of collagen of mammals in an aqueous solution is about 38° C. while denaturing temperature of collagen of fishes is generally lower than that of mammals and particularly, in some cases of collagens of fishes in cold currents such as salmon, the denaturing temperature is less than 20° C.

Collagen, for its excellent properties such as property of promoting adhesion and growth of cells, low antigenic property, high affinity for living organisms and biodegradable property, is advantageously used in various uses such as materials for cell experiments and medical materials. When used for such purposes, collagen is formed into various forms such as cotton-like product, film, sponge and gel depending upon the use. As preferable examples, for hemostatic material, collagen is used in form of cotton-like product, and for artificial skin, in form of sponge. Further, for cell experiments material, collagen is used in form of gel. However, collagen materials as such are usually in an aqueous state, fragile and less stretchable and therefore, in some cases, there are some limitations on application of such material to uses in cell experiment materials and medical materials.

For example, in recent years, it has been pointed out that characteristics of cells in an ordinary static incubation system (in vitro) are different in many respects from those in the system which receives mechanical stimulation in vivo and there has been an increasing demand for a cell experiment apparatus which gives mechanical stimulation easily and simply. For such a cell experiment apparatus, a cell carrier having both cell adhesion and stretching property is necessary and, for example, silicone membrane where fibronectin as a cell adhesion protein is coated is used (*Am. J. Physiol.* 274 (5 Pt 2), H 1532-1538 (1998)). However, many cells use collagen as a main footing in vivo and, in order to endow an in vivo-like environment to such cells, it is preferred to prepare a cell carrier using collagen. However, a stretching property is poor in conventional collagen materials and application of such a material to cell experiment apparatuses where mechanical stimulation is given is difficult.

In artificial skin for example, collagen sponge is favorably used for the purpose of endowing an environment suitable for healing the wound site to thereby promote tissue repair. However, conventional collagen sponge is poor in its stretching property and, when applied to wound sites on or around joints, the sponge is broken in some cases. Moreover, such a collagen sponge lacks strength for suture when applied to the wound site, therefore use of such a sponge involves troubles of using synthetic polymer in combination (JP-A-2001-104346) and the like. Furthermore, such a synthetic polymer is necessarily removed after the wound is healed and, at that time, the cured site receives some damages again.

As for artificial blood vessel, for example, in consideration for biocompatibility and antithrombotic property, an artificial blood vessel model of a hybrid type with an artificial tubular structure containing smooth muscle and having a flat lumen surface whereon a layer of endothelial cells may be formed.

As a specific model thereof, a model formed by molding gel-like collagen with smooth muscle mixed therein into a tubular structure is proposed (*Science*, 231, pages 397-400 (1986); *ASAIO Journal*, pages 383-388 (1994)). According to this model, artificial blood vessel having a flat lumen surface can be formed within a short period of time. However, such a product of tubular structure is fragile, and its strength is so low that the product immediately after manufactured may be broken if picked up with tweezers, and therefore there is a problem that such an artificial blood vessel cannot endure biomechanical environment present in living organisms.

In view of the above, another model is also proposed in which a culture liquid containing smooth muscle cells is directly sown on a biodegradable or non-biodegradable tubular structure having a relatively high mechanical strength and, after cultured until the lumen surface becomes flat, endothelial cells are sown (JP-A-2001-78750 (European Patent Laid-Open No. 1,214,952)). Such a model has a good mechanical strength and can be used as artificial blood vessel even for an artery. However, it is known that biodegradable or non-biodegradable tubular structure has a strong hydrophobicity and that its properties for adhesion and growth of cells are significantly bad. Therefore, there is a problem that it takes a long period of times of several months to culture the smooth muscle cells in the tubular structure until a flat lumen surface is formed. Such a problem makes the proposed model impractical in light of the situation where patients need artificial blood vessels. In addition, in the model, there remains another problem that, due to its low stretching property, abrasion takes place between the artificial vessel and inherent blood vessel after transplantation, a break is resulted at the bonding area and blood may leak out therefrom.

The above-mentioned problems are expected to be solved by imparting both stretching property and high mechanical strength to a collagen material. However, no collagen material having such properties and production method therefor has been disclosed.

Moreover, conventionally, most collagen serving as starting material for collagen materials, is collected from tissues of livestock, such as oxhide. However, BSE (bovine spongiform encephalopathy) have emerged in recent years and the risk of possible infections of pathogen to humans through the use of such collagen products containing materials derived from livestock including those derived from oxhide has been latently pointed out. Therefore, in view of safety and amount of sources, collagen derived from fishes has been suddenly receiving public attention as materials for cosmetics and for food and it is becoming important to use fish collagen having a low denaturing temperature as a starting material for collagen gel. However, although the risk involved in using collagen derived from fishes is low, due to its low denaturing temperature, its heat stability as a material is often insufficient. Therefore, for a starting material for a cell carrier and for a medical material, fish collagen is considered to be disadvantageous as compared with collagen derived from livestock.

The above-mentioned problems in conventional collagen materials such as insufficient stretching property and insufficient strength have been hindering a wide application of common livestock-derived collagen to a cell carrier or a medical material. In addition, there has been no satisfactory method for manufacturing medical materials where heat stability at least at 37° C. is required by using fish collagen.

SUMMARY OF THE INVENTION

Accordingly, an object of the invention is to provide a collagen material particularly derived from fishes which can be widely used as a cell carrier and a medical material and has excellent stretching property and mechanical strength and also to provide a method of manufacturing the same.

Conventional collagen materials are insufficient in stretching property and mechanical strength and, depending upon the use, such products are sometimes difficult to be used as a cell carrier or a medical material. In addition, there has been no satisfactory method for manufacturing a medical material where heat stability at least at 37° C. is required by using fish collagen.

As a result of intensive studies in order to overcome the above problems, the present inventors have succeeded in the manufacture of a collagen material having both stretching property and high mechanical strength by thermally treating a gel comprising collagen fiber cross-linked by a cross-linking agent, which manufacture could not be achieved in conventional methods. In addition, the present inventors have found the product extremely useful as a cell carrier and a medical material, and thus completed the invention. That is, the invention provides the following collagen material, a method for manufacturing the same and a cell carrier and a medical material using the collagen material.

1. A stretchable collagen material.
2. The stretchable collagen material according to the above 1, wherein the collagen is derived from fish.
3. The stretchable collagen material according to the above 1 or 2, wherein the collagen is cross-linked by using a cross-linking agent.
4. The stretchable collagen material-according to the above 3, wherein the cross-linking agent is a water-soluble carbodiimide.
5. A method for manufacturing a stretchable collagen material including a step in which gel comprising collagen fiber cross-linked by using a cross-linking agent is subjected to a thermal treatment.
6. The method for manufacturing a stretchable collagen material according to the above 5, including a step in which the gel is prepared by mixing of a collagen solution with a solvent which induces fiber formation and a solution of cross-linking agent.
7. The method for manufacturing a stretchable collagen material according to the above 5 or 6, including a step in which the gel is prepared by cross-linking of fibers by a cross-linking agent during the fibril formation process of collagen.
8. The method for manufacturing a stretchable collagen material according to any one of the above 5 to 7, wherein fish-derived collagen is used.
9. The method for manufacturing a stretchable collagen material according to the above 6, wherein the solvent inducing fiber formation is an aqueous solution of salt having a buffering ability selected from phosphate, acetate, carbonate and Tris.
10. The method for manufacturing a stretchable collagen material according to the above 6, wherein a solution in which a water-soluble carbodiimide is dissolved in the solvent inducing fiber formation is used as the cross-linking agent.
11. The method for manufacturing a stretchable collagen material according to the above 6, wherein the collagen concentration in the collagen solution is within a range of 0.01 to 3.0 (w/v) %.
12. The method for manufacturing a stretchable collagen material according to the above 6, wherein the concentration of the cross-linking agent used is within a range of 15 mM to 80 mM as the final concentration in collagen gel before the thermal treatment.
13. The method for manufacturing a stretchable collagen material according to the above 7, wherein mixing of the collagen solution with the solvent inducing fiber formation and the cross-linking agent solution is conducted at a temperature not higher than the temperature of the denaturing temperature of collagen plus 5° C.

14. The method for manufacturing a stretchable collagen material according to the above 7, wherein the gel is prepared by mixing the collagen solution, the solvent inducing fiber formation and the cross-linking agent solution and then conducting incubation at least for one hour at a temperature not higher than the temperature of the denaturing temperature of collagen plus 5° C.

15. The method for manufacturing a stretchable collagen material according to any one of the above 5 to 14, wherein the temperature for the thermal treatment is within a range of 30 to 200° C.

16. A stretchable collagen material which is manufactured by the method described in any one of the above 5 to 15.

17. The stretchable collagen material mentioned in any one of the above 1 to 4 and 16, which is used as a cell carrier for giving elastic stimuli to incubated cells.

18. A cell carrier or a medical material comprising the stretchable collagen material mentioned in any one of the above 1 to 4 and 16.

19. A basic material for artificial blood vessel comprising the stretchable collagen material mentioned in any one of the above 1 to 4 and 16.

20. Collagen used for a subcutaneous implant in cosmetic surgery, comprising the stretchable collagen material described in any one of the above 1 to 4 and 16.

21. A basic material for artificial tendon, comprising the stretchable collagen material described in any one of the above 1 to 4 and 16.

22. An artificial dura matter, comprising the stretchable collagen material described in any one of the above 1 to 4 and 16.

The collagen material prepared by the method of the invention is bestowed with excellent stretching property and mechanical strength without deteriorating a cell adhesion property of collagen. Therefore, application to the uses, where conventional collagen material cannot be applied due to insufficient stretching property or insufficient mechanical strength, is expected and furthermore, collagen derived from fishes having a low denaturing temperature can be employed as a starting material.

The major object of the invention is to provide a method for producing a rubber-like collagen material having excellent stretching property and mechanical strength, wherein a gel comprising collagen fiber cross-linked by a cross-linking agent is subjected to a thermal treatment and the collagen material thereby produced.

The invention will be illustrated in detail below.

With regard to type of collagen used in the invention, although there is no particular limitation so far as it has a fiber forming ability, collagen of type I showing a high yield or collagen comprising type I as the main component is preferred in view of industrial application.

With regard to molecular structure of collagen used in the invention, there is no particular limitation so far as it has a fiber forming ability. There is a report that non-helical region (telopeptide) existing at both ends of collagen molecule has antigenicity. Although there may be some cases where such a region is to be removed depending upon the use, it does not matter whether or not the telepeptide is removed, so far as a fiber forming ability is available.

With regard to denaturating of collagen used in the invention, there is no particular limitation so far as it has a fiber forming property. It is known that, even collagen once denatured can partially restore the helical structure of collagen to recover the fiber forming property. In order to achieve the invention, it is preferred that its helical rate (%) is 50 or more in view of the fiber forming property. The above-mentioned helical rate (%) has the same meaning as the recovery rate (%) of the helical structure mentioned in *Journal of Food Chemistry*, 60, page 1233 (1995). Thus, it stands for a recovery rate (%) of helix calculated from specific rotation measured by a polarimeter.

With regard to the origin of collagen used in the invention, although there is no particular limitation so far as it has a fiber forming property, collagen derived from the corium of vertebrate animals is used preferably in view of amount of resources and yield of collagen. Collagen derived from the corium of fishes, such as salmon skin, shark skin, tuna skin, cod skin and flounder skin, where possibility of containing pathogenic substances such as BSE is latently lower than that in livestock-derived collagen, is more preferably used and particularly preferably, salmon skin is used.

Collagen fiber in the invention means a filamentary structure as shown in pictures by a scanning electron microscope in *Journal of Agricultural Food Chemistry*, 48, pages 2028-2032 (2000).

With regard to the cross-linking agent used in the invention, there is no particular limitation so far as it can cross-link a protein and is soluble in water. Cross-linking agents are mentioned in detail in *Biomaterials*, 18, pages 95-105 (1997). Among them, cross-linking agents of aldehyde type, carbodiimide type, epoxide type and imidazole type are used preferably in view of economical efficiency, safety and operability. It is particularly preferable that water-soluble carbodiimide such as 1-ethyl-3-(3-dimethylaminopropyl) carbodiimide hydrochloride and 1-cyclohexyl-3-(2-morpholinyl-4-ethyl)carbodiimide sulfonate be used in a form of a solution in a solvent inducing a fiber formation as described later.

When a cross-linking agent used in the invention is a water-soluble carbodiimide, the cross-linking efficiency can be enhanced by coexistence of N-hydrodxysuccinimide.

A method for manufacturing the stretchable collagen according to the invention is characterized by a step where a gel comprising collagen fiber cross-linked by a cross-linking agent is subjected to a thermal treatment. With regard to specific examples of methods for preparation of the gel comprising collagen fiber cross-linked by a cross-linking agent, the following four methods are listed.

A: A method where a collagen solution and a solvent inducing fiber formation are mixed to prepare a gel comprising collagen fiber and the gel is dipped in a solution of cross-linking agent to cross-link the collagen fiber.

B: A method where a collagen solution is mixed with a solution of cross-linking agent in a solvent inducing fiber formation.

C: A method where a collagen solution is mixed with a solvent inducing fiber formation and a solution of cross-linking agent is added thereto either simultaneously or thereafter.

D: A method where a solution of cross-linking agent is added to a collagen solution and, after that, a solvent inducing fiber formation is mixed therewith.

According to such methods, a collagen gel comprising cross-linked collagen fiber is prepared.

Particularly in the methods B to D, cross-linking is introduced not only onto the surface of collagen fiber but also into collagen fiber, whereby collagen gel which can give collagen materials having excellent stretching property and mechanical strength is manufactured. In view of operability, it is particularly preferred to prepare a collagen gel by the method B.

In the method for manufacturing stretchable collagen material according to the invention, pH of a collagen solution used for preparing collagen gel varies depending upon the method for manufacturing collagen material. Collagen is roughly divided into collagen solubilized with acid which is extracted with an acidic aqueous solution and collagen solubilized with alkali which is extracted with an alkaline aqueous solution. When the collagen used in the invention is a collagen solubilized with acid, its pH is preferably within a range of 2.0 to 6.0. When the pH value is lower than 2.0, there may be cases where collagen molecules are hydrolyzed, which is not preferred. When the pH value exceeds 6.0, there may be cases where collagen is not sufficiently solubilized, which is not preferred. On the other hand, when the collagen used in the invention is a collagen solubilized with alkali, its pH is preferably within a range of 5.5 to 10.0. When pH is lower than 5.5, there may be cases where collagen is not sufficiently solubilized and that is not preferred. When the pH value exceeds 10, there may be cases where collagen molecules are hydrolyzed, which is not preferred.

With regard to a solvent for a collagen solution used in preparing collagen gel in the method for manufacturing a stretchable collagen material according to the invention, in the case of an acidic solvent, it is preferred to use those widely used in industry, for example, water and an aqueous solution of hydrochloric acid, acetic acid, citric acid, fumaric acid, for safety in view of the final use of the product. In the case of a solvent which is neutral to alkaline, it is preferred to use water or an aqueous solution of phosphate, acetate, Tris, etc. for the same reason as in the case of acidic solvent.

With regard to the solute concentration in the collagen solvent used for preparing collagen gel in the method for manufacturing stretchable collagen material according to the invention, there is no particular limitation so far as the solvent can obtain a pH value at which the collagen used is solubilized. However, when the solute concentration is too high, depending on the solute used, there may be some cases where the solvent cannot obtain a pH value of the aimed range, where fiber formation of collagen is inhibited and where properties of the resulting gel such as cell adhesive property are deteriorated, which are unpreferable. Preferably, the concentration is 1.0 M or less and, more preferably, 0.50 M or less.

In a method for manufacturing a stretchable collagen material according to the invention, for the purpose of enhancing the functions of collagen gel, various functional substances may be added to a collagen solution used for preparing the collagen gel to the extent that the effects of obtaining a collagen gel with high heat stability according to the invention are not inhibited. Specific examples thereof include functional proteins such as cell growth factor, hyaluronic acid, chondroitin sulfate, polylactic acid, β1-3 glucan, chitin, chitosan and other functional polysaccharide.

It is preferable that the concentration of collagen in a collagen solution used in preparing collagen gel in a method for manufacturing a stretchable collagen material according to the invention be within a range of 0.01 to 3.0 (w/v) % in view of solubility of collagen, viscosity of solution or property of gel. When the concentration is lower than 0.01 (w/v) %, the strength of the resulting gel may be insufficient in some cases, which is not preferred. When the concentration exceeds 3.0 (w/v) %, viscosity of the collagen solution is so high that manufacture of gel may become difficult, which is not preferred. Preferably, it is within a range of 0.05 to 2.0 (w/v) %.

With regard to the concentration of a cross-linking agent used in preparing collagen gel in a method for manufacturing a stretchable collagen material according to the invention, the final concentration of cross-linking agent in the resulting collagen gel is important rather than the concentration of the cross-linking agent solution. The final concentration is preferably within a range of 15 mM to 80 mM as the final in view of the cross-linking degree and the cross-linking rate. When the final concentration of the cross-linking agent is lower than 15 mM, the cross-linking degree is insufficient, resulting in lowering the stretching property and mechanical strength of the collagen material in some cases, which is not preferred. When the final concentration of the cross-linking agent exceeds 80 mM, fiber formation of collagen may be significantly inhibited by co-existence of the cross-linking agent, resulting in lowering stretching property and mechanical strength of the collagen material in some cases, which is not preferred.

With regard to a solvent inducing fiber formation of collagen used in preparing collagen gel in a method for manufacturing a stretchable collagen material according to the invention, there is no particular limitation. However, in consideration for the final uses such as cell carrier and medical material, it is preferred to use those widely used in industry, for example, an aqueous solution of salt having a buffering property such as phosphate, acetate, carbonate and Tris which has no or low cytotoxicity. Although the pH suitable for fiber formation of collagen varies depending upon the type of collagen, in many cases, it is within a range of pH 5 to 9 and, within the said range, a phosphate having a high buffering ability is used particularly preferably. The solute concentration in the solvent is in accordance with the above-described solute concentration in a solvent for collagen solution used in manufacturing the collagen gel.

In the method for manufacturing a stretchable collagen material according to the invention, the operation of mixing a collagen solution with a solution inducing fiber formation or with a cross-linking agent solution is carried out in such a manner that the temperature of each of those solutions is kept at a temperature not much higher than the denaturing temperature of the collagen. Particularly, the temperature of the resultant mixed solution is important. When the temperature of the mixed solution is much higher than the denaturing temperature of collagen, although the cross-linking reaction takes place, collagen is denatured and its fiber forming ability is reduced, whereby the stretching property of the resulting collagen material is deteriorated, which is not preferred. Preferably, the temperature is the denaturing temperature of collagen used +5° C. or lower, more preferably, it is the denaturing temperature of collagen used or less.

The above denaturing temperature of collagen is a value determined based on changes in rotary power of a collagen solution when the collagen solution is gradually heated, according to description in *Journal of Food Chemistry*, 60, page 1233 (1995).

In an operation for mixing various solutions such as solution inducing fiber formation and solution causing cross-linking reaction with a collagen solution, there is no particular limitation on the mixing method. However, it is preferable that the solutions be mixed as uniform as possible before fluidity of the mixed solution is lost by gel formation of the solution through fiber formation. A method where the mixed solution is placed in a container and the container is shaken by hand or by a shaker and a method where the solution is mechanically stirred using a magnetic stirrer or a stirring stick equipped with wings are preferably employed.

After various solutions inducing fiber formation and cross-linking are mixed with the collagen solution, the resulting mixed solution is incubated so that fiber formation and cross-linking reaction sufficiently take place. The incubating time is preferably one hour or more in the light of obtaining high gel strength or heat stability. In view of prevention of denaturation of collagen, the temperature for the incubation is preferably the denaturing temperature of collagen +5° C. or lower, and more preferably the denaturing temperature of collagen or lower.

By subjecting the gel comprising collagen fiber cross-linked by using a cross-linking agent prepared by the above-mentioned method to a thermal treatment, the gel shrinks by heat, thereby the stretchable collagen of the invention is prepared.

In a method for manufacturing a stretchable collagen material according to the invention, the temperature of the thermal treatment is from 30 to 200° C. When it is lower than 30° C., reforming of collagen gel into a stretchable collagen material does not take place. The higher the temperature, the shorter the time required for reforming. When the temperature is too high, collagen is dissolved and properties of the resulting collagen material may be deteriorated. Preferably, it is within a range of 40 to 150° C. and more preferably within a range of 50 to 100° C.

In the method for manufacturing a stretchable collagen material according to the invention, the thermal treatment time (x) varies depending upon the temperature for the thermal treatment and the operation is conducted within a range which satisfies the condition of $t \leq -14x+200$ (t: temperature (° C.) for thermal treatment; x: time (hour (s)) for thermal treatment). In a condition of $t > -14x+200$, collagen is dissolved and properties of the resulting collagen material may be deteriorated. Preferably, the time period for the thermal treatment (x) is in a range which satisfies the condition of $t \leq -14x+114$.

With regard to the method of thermal treatment for collagen gel in a method for manufacturing a stretchable collagen material according to the invention, there is no particular limitation, so far as the collagen gel can obtain the target temperature without being dried. However, since the dominant constituent of the collagen gel to be heated is water, it is preferred to heat it in an aqueous solution or by a wet-type oven. When heating is conducted by a dry-type oven or the like, the collagen material may be dried and the stretching property may be deteriorated.

An additional cross-linking may be carried out for further enhancement of mechanical strength and heat stability of the stretchable collagen material prepared by the above-mentioned method. The additional cross-linking is conducted by dipping the stretchable collagen material in an aqueous solution of cross-linking agent.

Type and concentration of a cross-linking agent used for the introduction of additional cross-linking are in accordance with type and concentration of the cross-linking agent used for the preparation of the aforementioned collagen gel.

Solvent for an aqueous solution of a cross-linking agent used for the introduction of additional cross-linking is in accordance with the solvent of the cross-linking agent used for the preparation of the aforementioned collagen gel.

The stretchable collagen material prepared by the above-mentioned method has excellent stretching property and high mechanical strength and, at the same time, it has excellent heat stability as well. Therefore, application to uses, to which conventional collagen materials cannot be applied, is expected and, further, collagen derived from fishes having low denaturing temperature can be advantageously used as starting material.

BRIEF DESCRIPTION OF THE DRAWINGS

FIG. 3 is a photographic image of the collagen material of the Example after elongation.

FIG. 4 is a state of cell adhesion on the collagen material of the Example.

DETAILED DESCRIPTION AND BEST MODE FOR CARRYING OUT THE INVENTION

Figure 1:
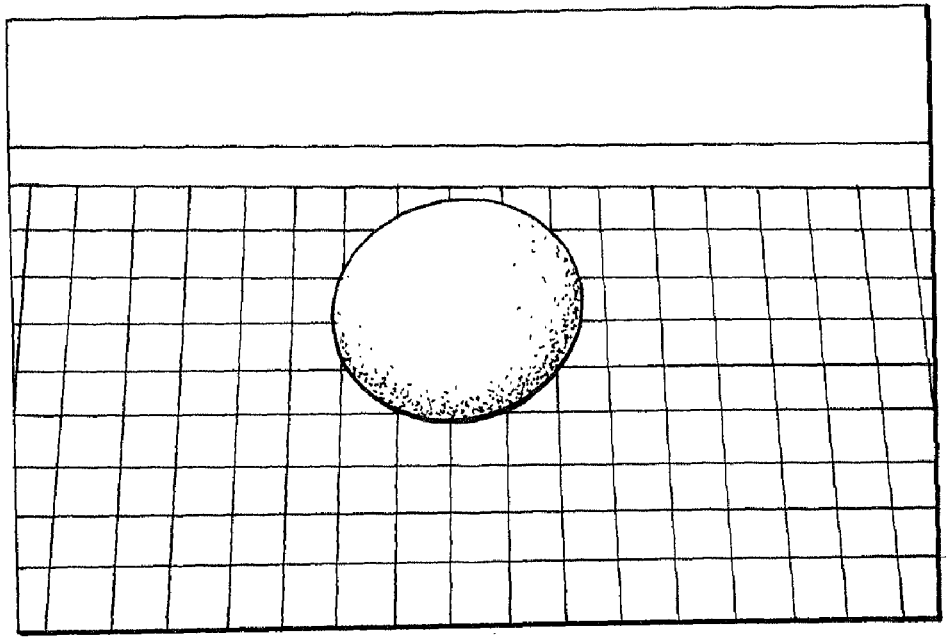
FIG. 1 is a photographic image of a collagen material of the Example before elongation.

The invention will now be more specifically illustrated by way of the Example although the invention is not limited to the scope mentioned hereinafter.

Firstly, methods for measurement on various properties of the collagen material prepared in the Example will be shown.
1. Measurement of Breaking Elongation and Breaking Tenacity of Collagen Material Breaking elongation and breaking tenacity of collagen material were determined according to the following operations.

A test piece having a rectangular form of 10 mm width and 1.2 mm thickness was fixed at its both ends using chucks and pulled at the rate of 60 m/minute and elongation (%) and stress (g) upon breaking were measured using a rheometer (CR-200D; manufactured by Sun Scientific Co., Ltd.). Each measurement was conducted for five test pieces and a mean value thereof was calculated.
2. Evaluation of Stretching Property of Collagen Material Stretching property of collagen material was evaluated according to the following operation.

An end of a circular test piece having an inner diameter of 23 mm and thickness of 1.2 mm was held down with a finger, and the opposite end thereof was pulled upward with flat tweezers so that the length of the long axis of the test piece assuming an elliptic shape could be 50 mm. After the test piece was kept in that state for 5 seconds, the tweezers were detached from the test piece and the shape of the test piece was observed.
3. Observation of Cell Adhesion to Collagen Material (1) Cell Culture on Collagen Material Commercially available osteoblasts (manufactured by Clonetics Corp.) were incubated in an MEMα modified medium (manufactured by Nissui Pharmaceutical Co., Ltd.; hereinafter, abbreviated as α-MEM) to which 10% of serum (fetal bovine serum; manufactured by Gibco) was added. The medium was exchanged every two days and, when the medium became semiconfluent, the cells were detached using a solution of 0.02% trypsin-0.25% EDTA and successive subculture was conducted by making the cell numbers in each new plate $5 \times 10^3$ cells/cm$^2$.

In the incubation of collagen material, osteoblasts of passage number from 5 to 10 were used. The collagen material was dipped for sterilization in a 70% aqueous solution of ethanol for 24 hours before the incubation. The collagen material was placed on a polystyrene Petri dish having an inner diameter of 10 mm (with 24 wells; manufactured by Nalge Nunc International K.K.) for incubation of cells. α-MEM (1 ml) was added thereto and, after incubating at 37° C. for 1 hour, the medium was removed. This procedure was repeated once again and the collagen material was substituted with a medium. After that, $1 \times 10^4$ cells of osteoblasts were sowed on the collagen material and incubation was conducted at 37° C. in a 5% $CO_2$ incubator using an α-MEM as a medium.

(2) Observation by SEM

The collagen material incubated for 2 days was twice washed with 1 ml of a phosphate-buffered saline (PBS). After washing, it was dipped for 1 hour in 1 ml of a solution of a 2.5% glutaraldehyde-PBS to fix the cells. After fixing, washing was conducted twice with 1 ml of aseptic water. The product was dipped in aqueous solutions of ethanol concentrations were 50%, 60%, 70%, 80% and 90% successively in this order for 20 minutes each. Subsequently, the product was dipped in 100% ethanol twice for 20 minutes each time and water was completely removed. Further, after dipped in isoamyl acetate twice for 20 minutes each time and then $CO_2$ critical point drying was conducted. On the sample which had been subjected to the critical point drying, gold was vapor-deposited using an ion coater (E-1010; manufactured by Hitachi Ltd.), to thereby prepare a sample to be observed by a scanning electron microscope (SEM). Observation by an SEM was conducted at a magnification of 15,000 using JSM-6500F manufactured by JEOL.

EXAMPLE

Figure 2:
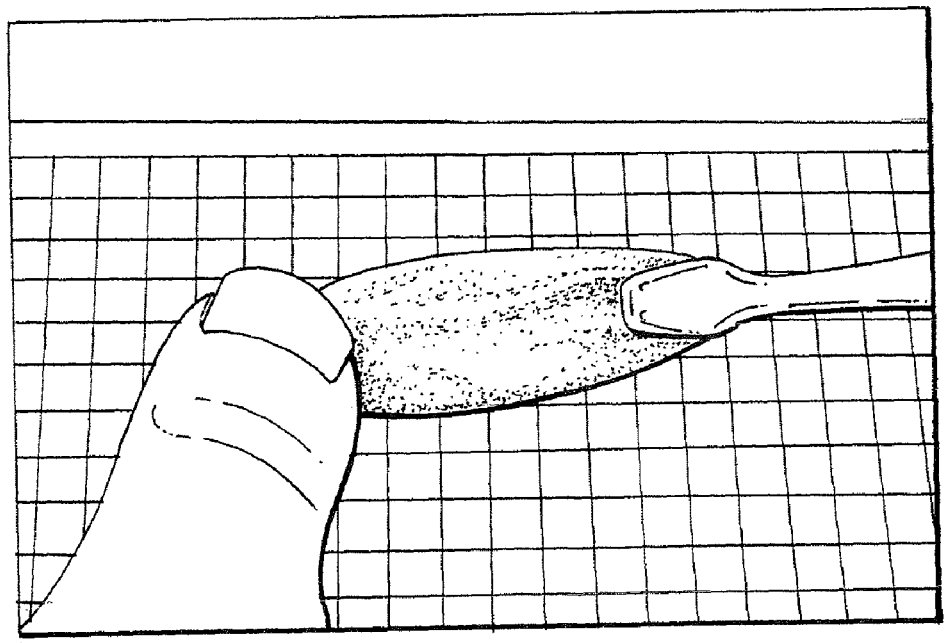
FIG. 2 is a photographic image of a collagen material of the Example during elongation.

1. Manufacture of Soluble Collagen from Fish Skin
   (1) Defatting of Salmon Skin
   As a fish skin, the skin of salmon (*Oncorhynchus Keta*) was used. Scales and flesh were removed from the salmon skin by a surgical knife and the skin was finely cut into about 3 cm square each. The pieces were defatted with a mixed solvent comprising chloroform/methanol (1/1) 3 times, then washed with methanol twice to remove chloroform and then washed with water 3 times to remove methanol. All steps hereinafter were conducted at 4° C.
   (2) Extraction of Collagen and Digestion with Pepsin
   The above-prepared defatted salmon skin (130 g) was dipped in 5 L of 0.5M acetic acid of 4° C. and allowed to stand for 4 days. The swollen salmon skin was filtered using medical gauze and the filtrate was centrifuged at 10,000×g for 30 minutes to precipitate an insoluble matter, and 1.5 L of supernatant liquid was recovered. The supernatant liquid was mixed with 50 mg of pepsin powder and the mixture was gently stirred for 2 days.
   (3) Purification of Collagen
   Sodium chloride was added to the above collagen solution so as to make the final concentration 5% and the mixture was gently stirred using a glass rod for 1 minute and allowed to stand for 24 hours. A white insoluble matter generated by salting-out was centrifuged (under the same condition as above) to recover the precipitate and the precipitate was added to 2 L of 0.5 M acetic acid and dissolved therein by gentle stirring. Dissolution took 3 days. Such an operation was repeated once again to give a colorless and transparent collagen solution. The collagen solution was dialyzed against deionized water using a cellulose tube. Deionized water was repeatedly exchanged until pH of the outer liquid of dialysis became neutral and the resulting neutral collagen solution was freeze-dried. A white sponge-like collagen was obtained.
2. Manufacture of Collagen Gel
   (1) Preparation of 0.50% Aqueous Solution of Collagen
   The above-prepared sponge-like collagen was dried under reduced pressure in a desiccator containing silica gel therein, precisely weighed, added to diluted hydrochloric acid of pH 3.0 previously cooled at 4° C. so as to make 0.50 (w/v) % and gently stirred to dissolve. Subsequently, a collagen solution was filtered through membrane filters having pore sizes of 10 μm, 0.65 μm and 0.45 μm successively in this order. The filtrate was divided into 20 mL portions and each portion was placed in a centrifugal tube (50 mL) made of polypropylene.
   (2) Preparation of Aqueous Solution of a Cross-Linking Agent
   A 100 mM aqueous solution of 1-ethyl-3-(3-dimethylaminopropyl)carbodiimide hydrochloride was prepared using as a solvent, a 30 mM aqueous buffer solution of sodium phosphate of pH 6.8 containing 70 mM of sodium chloride. The aqueous solution of the cross-linking agent thus obtained was divided into 20 mL portions and each portion was placed in a centrifugal tube (50 mL) made of polypropylene.
   (3) Manufacture of Collagen Gel
   All of the following operations were conducted at 8° C. The above-prepared cross-linking agent solution (20 mL) was added to the centrifugal tube where the above-prepared 0.50% aqueous solution of collagen (20 mL) was placed and a lid was put on the tube. The solutions were mixed by shaking the centrifugal tube and the content was poured onto a polystyrene Petri dish of 10 cm inner diameter for cell incubation so as to make the depth of the solution 6 mm and allowed to stand for 24 hours, to thereby obtain a collagen gel.
3. Manufacture of a Stretchable Collagen Material by a Thermal Treatment of Collagen Gel
   The above collagen gel was dipped in hot water of 80° C. The gel started to shrink and, after about 2 minutes, the shrinking ceased. After allowed to further stand for 1 minute, the resultant collagen was taken out as a stretchable collagen material of the Example. The resulting stretchable collagen material had a circular form of an inner diameter of 23 mm and a thickness of 1.2 mm.
4. Breaking Elongation and Breaking Tenacity
   Breaking elongation and breaking tenacity of the stretchable collagen material measured by the aforementioned methods were 338 (%) and 77.6 (g), respectively.
5. Evaluation of Stretching Property of the Collagen Material
   Stretching property of the collagen material was evaluated by the aforementioned method. The sample of 23 mm inner diameter having a circular form was pulled upward until the length of the long axis of the ellipse became 50 mm and, after that, the inner diameter got back to 24 mm which was nearly the same as the diameter before elongation. The collagen material before the elongation, the collagen material during the elongation and the collagen material after the elongation are shown in FIGS. 1 to 3, respectively.
6. Observation of Cell Adhesion to Collagen Material
   A picture under an SEM is shown in FIG. 4. Osteoblasts were adhered to the collagen material in a high density.
   As will be apparent from the measured data for breaking elongation and breaking tenacity, the stretchable collagen material of the invention shows excellent elongation and tenacity, like rubber. As will be apparent from FIGS. 1 to 3, the stretchable collagen material of the invention has an excellent stretching property. Those results show that the present invention enables manufacture of a collagen material having stretching property and tenacity like rubber.
   As will be apparent from FIG. 4, the stretchable collagen material of the invention has an excellent cell adhesion property. The result shows that the collagen material of the invention can be advantageously used as a base material for a cell carrier or for a medical material.
7. Preferred Embodiments of the Invention
   While there may be other embodiments of the invention that will be preferred by those reading this application, the following is the best mode known to the inventors for carrying out the invention.
   An isolated collagen of type I, as described generally above, was prepared. However, the property of breaking elongation was engineered to fall within specific ranges as follows. These collagens have a breaking elongation of from 2.5 to 4.0 times of the original length. By this we mean for every unit of length, the unit can be stretched one and one half times (1 unit+1.5 units=2.5 units=breaking elongation of 2.5 times) for the lower value. A similar relationship exists for the upper value. Expressed as a breaking elongation %, this would be 150% to 300%.

Within this broad range of preferred embodiments, there are particularly preferred embodiments of breaking elongation of from 2.5 to 3.5 times of the original length; more particularly 2.5 to 3.0 times of the original length. Expressed as percentages these are 150% to 250% and 150% to 200%, respectively.

Having described my invention, it should be apparent that various modifications may be made by those skilled in the art, without departing from the scope of the appended claims.

The invention claimed is:

1. A stretchable material obtained by the method comprising the steps of:
   (a) first providing a collagen solution in which the collagen is dissolved in an aqueous solvent;
   (b) gelating the collagen solution by inducing fibril formation of the collagen;
   (c) cross-linking the collagen fibril by using a cross-linking agent; and,
   (d) thereafter subjecting the obtained cross-linked collagen fibril to heat treatment at a temperature in the range of 80° to 100° C.

2. The stretchable material of claim 1, wherein the step of gelating the collagen solution, and the step of cross-linking the collagen fibril, are performed by the step of bringing an aqueous collagen solution without making fibril formation, into contact with an aqueous phosphate solution which induces fibril formation, in the presence of a cross-linking agent, simultaneously.

3. The stretchable material of claim 1, wherein the cross-linking agent is a water-soluble carbodiimide.

4. The stretchable material of claim 1, obtained by conducting a second cross-linking step after the heat treatment step.

5. The stretchable material of claim 4, wherein the cross-linking agent used for the second cross-linking step is a water-soluble carbodiimide.

6. The stretchable material of claim 1, having a stretching property such that the inner diameter of a disk-shaped piece of material, originally having an inner diameter of 23 mm and a thickness of 1.2 mm, returns to 24 mm or less after being stretched until a longitudinal axis of the elliptical shape of the stretched material is 50 mm.

7. The stretchable material of claim 1, wherein the collagen is derived from fish.

8. An embeddable material to be embedded in the living body comprising the stretchable material of claim 1.

9. An artificial blood vessel comprising the stretchable material of claim 1.

* * * * *